United States Patent [19]

Berlin

[11] Patent Number: 4,630,466
[45] Date of Patent: Dec. 23, 1986

[54] APPARATUS FOR TESTING ROD-SHAPED ARTICLES OF THE TOBACCO PROCESSING INDUSTRY

[75] Inventor: Herbert Berlin, Hamburg, Fed. Rep. of Germany

[73] Assignee: Hauni-Werke Körber & Co. KG., Hamburg, Fed. Rep. of Germany

[21] Appl. No.: 657,007

[22] Filed: Oct. 2, 1984

[30] Foreign Application Priority Data

Oct. 8, 1983 [DE] Fed. Rep. of Germany ....... 3336667

[51] Int. Cl.⁴ ............................................. G01M 3/04
[52] U.S. Cl. ........................................... 73/38; 73/49.8
[58] Field of Search ............................ 73/38, 41, 49.8

[56] References Cited

U.S. PATENT DOCUMENTS

| | | | |
|---|---|---|---|
| 3,386,281 | 6/1968 | Menge et al. | 73/38 X |
| 3,769,832 | 11/1973 | Baier | 73/38 X |
| 3,948,084 | 4/1976 | Heitmann et al. | 73/41 |
| 4,246,774 | 1/1981 | Flesselles et al. | 73/38 |
| 4,429,567 | 2/1984 | Koch et al. | 73/38 X |
| 4,528,841 | 7/1985 | Siems | 73/38 |

Primary Examiner—Stewart J. Levy
Assistant Examiner—Joseph W. Roskos
Attorney, Agent, or Firm—Peter K. Kontler

[57] ABSTRACT

A cigarette testing apparatus wherein the cigarettes are transported in axially parallel peripheral flutes of a testing drum toward, past and beyond a testing station. A wobble plate is adjacent to one end of and rotates with the drum and supports a set of sleeve-like elastic sealing elements each of which is slipped onto the adjacent end of a cigarette when it approaches the testing station. The sealing elements are surrounded by resilient annular clamping members which tend to reduce their inner diameters and automatically compel the respective sealing elements to sealingly engage the peripheries of the inserted ends of cigarettes at the testing station. Pivotable cams are provided on the wobble plate to expand the clamping members downstream of the testing station in order to permit extraction of the ends of tested cigarettes from the sealing elements and insertion of untested cigarettes into the respective flutes.

10 Claims, 4 Drawing Figures

APPARATUS FOR TESTING ROD-SHAPED ARTICLES OF THE TOBACCO PROCESSING INDUSTRY

BACKGROUND OF THE INVENTION

The present invention relates to improvements in apparatus for testing cigarettes and analogous rod-shaped articles of the tobacco processing industry. More particularly, the invention relates to improvements in apparatus of the type wherein rod-shaped articles of the tobacco processing industry are conveyed sideways (i.e., at right angles to their respective axes) toward, past and beyond a testing station at which their tubular wrappers are tested by one or more streams of air or another gaseous testing fluid.

Commonly owned U.S. Pat. No. 3,948,084, granted Apr. 6, 1976 to Heitmann et al., discloses a testing apparatus for cigarettes or like rod-shaped articles wherein the end faces of articles which approach the testing station are engaged by apertured sealing elements which serve to seal the end faces from the surrounding atmosphere as well as to provide paths for the admission of testing fluid into the respective ends of the wrappers. The sealing elements consist of rubber or a similar elastomeric material and are mounted on two carriers in the form of wobble plates which flank the drum-shaped conveyor for the articles and rotate therewith so that the sealing elements of the two carriers are in register with the adjacent ends of articles in the respective flutes at the periphery of the conveyor.

It is further known to provide specially designed means for ensuring that the sealing elements on the carriers of the testing apparatus will more reliably engage the adjacent ends of the articles to prevent uncontrolled leakage of testing fluid which could lead to distorted measurements and expulsion of satisfactory articles from the path wherein satisfactory articles are supposed to advance to storage, to a further processing station (e.g., into a filter tipping machine) or directly to a packing machine. Reliable sealing of the ends of articles at the testing station (so as to prevent uncontrolled escape of testing fluid) is especially desirable when the apparatus is used for the testing of filter cigarettes or filter rod sections having so-called climatic or ventilation zones with perforations which are supposed to admit predetermined quantities of cool atmospheric air into the column of tobacco smoke. The testing apparatus are supposed to monitor the permeability of such ventilation zones and to ensure segregation of all articles whose perforations admit excessive or insufficient quantities of air. Adequate sealing of the ends of cigarettes or filter rod sections against uncontrolled escape of testing fluid or uncontrolled penetration of atmospheric air is indispensable in connection with the testing of ventilation zones because even minor leaks are likely to greatly distort the results of measurements since the rate of flow of testing fluid through the perforations of a ventilation zone is very low.

A drawback of presently known testing apparatus wherein the sealing elements are forced into sealing engagement with the adjacent ends of the articles to be tested is that the complexity and cost of such apparatus are very high and also that the sealing action is not sufficiently reliable. For example, certain presently known apparatus employ axially shiftable sleeves which are slipped onto the sealing elements at or slightly ahead of the testing station. It was also proposed to move the sealing elements into engagement with the adjacent ends of rod-shaped articles by streams of air or another gaseous fluid. The provision of such devices in a testing apparatus for cigarettes or other rod-shaped articles of the tobacco processing industry contributes significantly to the initial and maintenance cost as well as to the bulk of the testing apparatus without, however, ensuring a highly predictable, reliable and reproducible sealing action.

OBJECTS AND SUMMARY OF THE INVENTION

An object of the invention is to provide a testing apparatus for rod-shaped articles of the tobacco processing industry wherein the sealing elements are movable into and from engagement with the articles to be tested in a novel and improved way.

Another object of the invention is to provide an apparatus wherein the articles are treated gently even if they are being tested at the rate at which they issue from a modern high-speed making machine.

A further object of the invention is to provide a testing apparatus which is much less likely to permit uncontrolled leakage of atmospheric air or testing fluid than heretofore known testing apparatus.

An additional object of the invention is to provide a testing apparatus which can be installed in existing tobacco and/or filter material processing machines as a superior substitute for heretofore known testing apparatus.

Another object of the invention is to provide novel and improved sealing elements for use in an apparatus of the above outlined character.

A further object of the invention is to provide the testing apparatus with novel and improved means for deforming sealing elements into engagement with and/or for permitting or causing disengagement of sealing elements from the ends of rod-shaped smokers' articles.

Another object of the invention is to provide a novel and improved method of sealing the ends of filter cigarettes or other rod-shaped smokers' articles during testing of their wrappers.

An additional object of the invention is to provide a filter tipping machine which embodies the above outlined testing apparatus.

A further object of the invention is to provide a testing apparatus which is simpler, more compact and more reliable than heretofore known testing apparatus.

The invention resides in the provision of an apparatus for testing rod-shaped articles of the tobacco processing industry wherein open-ended tubular wrappers surround fillers of tobacco and/or filter material. The apparatus comprises means (e.g., a rotary drum-shaped conveyor) for conveying a succession of rod-shaped articles sideways (at right angles to their respective longitudinal axes) past a testing station, elongated flutes or analogous receiving means provided on the conveying means for the articles, carrier means (e.g., a rotary wobble plate adjacent to one axial end of the drum-shaped conveyor) adjacent to one end of each receiving means and arranged to move with the conveying means, elastically deformable tubular sealing elements provided on the carrier means, one for each receiving means and each in register with the adjacent end of the article in the respective receiving means, means (e.g., suitably inclined bearings for the aforementioned wobble plate) for effecting a relative movement between the conveying means and the carrier means so that the ends of the articles at the testing station penetrate into the respective tubular sealing elements, substantially annular clamping members, one for each sealing element and each surrounding the respective sealing element, and actuating means for varying the diameters of the clamping members so as to urge the respective sealing elements into sealing engagement with the peripheral surfaces of the article ends therewithin during travel of the articles past the testing station.

In accordance with a presently preferred embodiment of the invention, the clamping members are resilient and exhibit a tendency to contract into deforming engagement with the respective sealing elements, and the actuating means then comprises means for effecting radial expansion of the clamping members while such clamping members are remote from the testing station. This allows for removal of freshly tested articles from their receiving means and for insertion of fresh (untested) articles into the thus emptied receiving means.

The clamping members can constitute annular bodies made of wire or metallic or plastic strip stock (such as conventional hose clamps) each of which has a first end portion anchored in or otherwise mounted on the carrier means and a second end portion which is movable relative to the first end portion to thereby increase or reduce the diameter of the respective clamping member. The actuating means then includes means for moving the second end portions of the clamping members relative to the respective first end portions. For example, the actuating means can comprise a discrete cam for each clamping member (the cam can be used to move the second end portion of the respective clamping member relative to the first end portion) and means for pivoting or otherwise moving the cams with reference to the carrier means. The means for moving the cams can comprise shafts, one for each cam, and means for rocking the shafts back and forth in response to movement of the carrier means. Such rocking means can comprise a discrete lever affixed to each of the shafts, a discrete roller or other suitable follower on each lever, and stationary cam means (e.g., on the aforementioned bearing for the wobble plate) which is tracked by the followers.

Each sealing element can constitute a length of flexible cylindrical hose.

Each sealing element can be provided with an apertured internal partition which is spaced apart from its open article-receiving end and abuts against the end of the inserted article during travel past the testing station. The partition can be used to facilitate other types of testing, for example, a determination whether or not the end faces of the articles are disposed in planes which are exactly normal to the longitudinal axes of such articles.

If the carrier means includes a wobble plate, such carrier means and the drum-shaped conveying means rotate about mutually inclined axes and the aforementioned movement effecting means preferably constitutes the bearing or bearings for the wobble plate; such bearing or bearings cause successive increments of the wobble plate (and hence successive sealing elements on the wobble plate) to approach the adjacent end face of the conveyor during travel toward the testing station and to move away from the adjacent end face of the conveyor during travel beyond the testing station.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
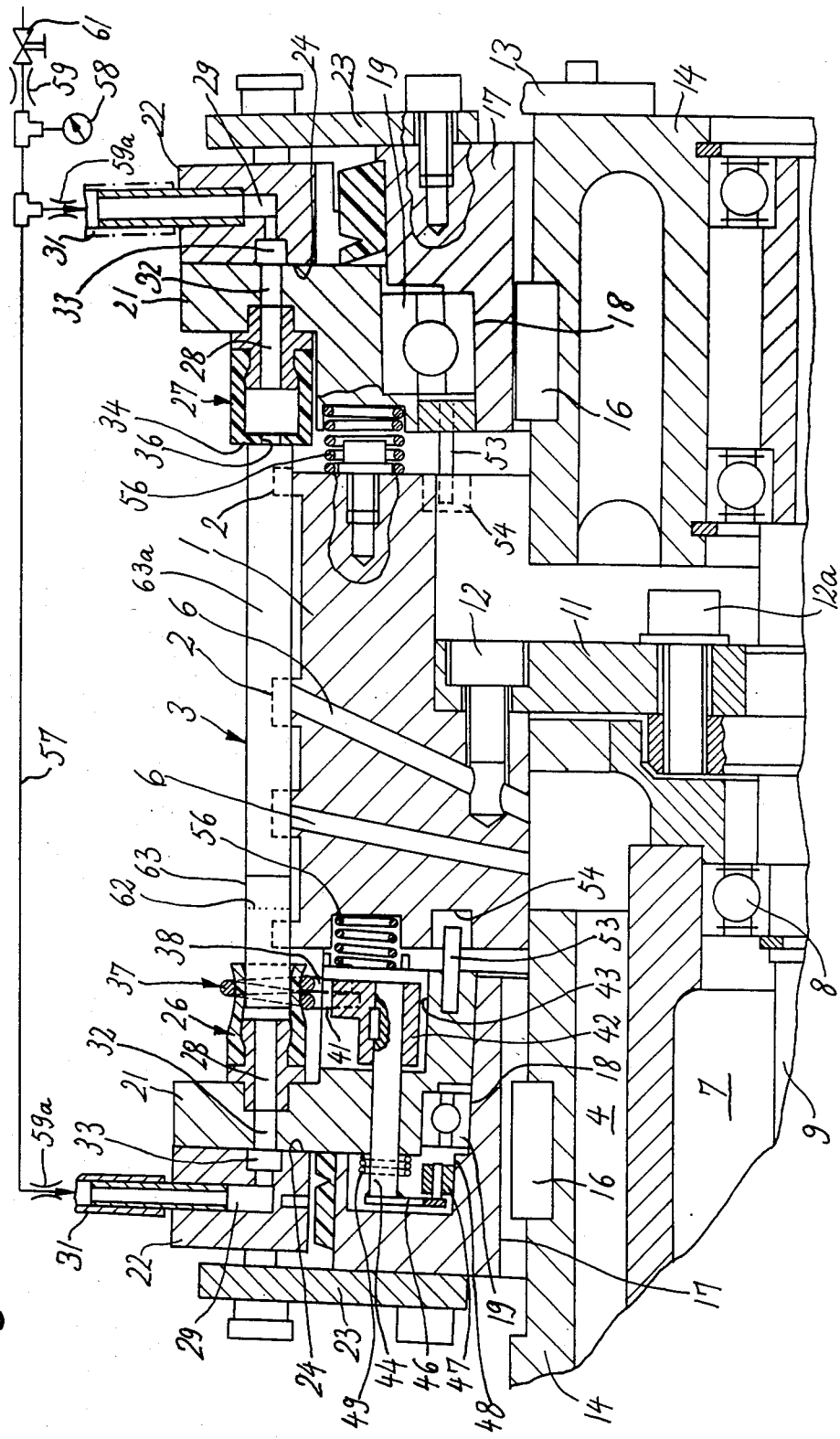
FIG. 1 is a fragmentary central longitudinal sectional view of a testing apparatus which embodies one form of the invention.

FIG. 1 shows a portion of a cigarette testing apparatus which is installed in a filter tipping machine, e.g., a machine known as MAX or MAX-S (both produced by the assignee of the present application). A MAX is described and shown in the aforementioned patent to Heitmann et al. whose disclosure is incorporated herein by reference. Reference may further be had to numerous U.S. patents of the assignee which also disclose testing apparatus for cigarettes or other types of rod-shaped articles of the tobacco processing industry.

The testing apparatus of FIG. 1 comprises a conveying means 1 which is a rotary drum-shaped conveyor having axially parallel peripheral flutes 2 constituting receiving means for rod-shaped articles 3 each of which is a filter cigarette of unit length having a tobacco-containing portion 63a, a filter tip 63 with perforations 62 constituting a climatic or ventilation zone, and a tubular wrapper whose ends are open and which surrounds a rod-like filler consisting in part of tobacco and in part of filter material. The purpose of the testing apparatus is to ascertain the condition of the tubular wrappers of the articles 3, i.e., whether or not such wrappers have open seams, leaks in the regions where the filter tips 63 are connected to the tobacco-containing portions 63a, frayed ends, holes and/or a combination of such defects. Furthermore, the testing apparatus is supposed to detect those articles 3 whose ventilation zones 62 permit the passage of excessive or insufficient quantities of atmospheric air.

Each receiving means or flute 2 can consist of several coaxial sections and the drum-shaped body of the conveyor 1 has substantially radially extending channels 6 serving to draw air from the respective flutes 2 while the flutes contain or are supposed to contain articles 3 so as to ensure that the articles are held in the flutes against the action of centrifugal force and/or gravity between a first transfer station where the flutes 2 receive untested articles from a preceding conveyor (not shown) and a second transfer station where the tested articles 3 leave the conveyor 1. The inner ends of certain channels 6 communicate with an axially extending channel 4 which is machined into a stationary shaft 7. The latter contains bearings 8 for a rotary drive shaft 9 which transmits torque to the cylindrical body of the conveyor 1 by way of a disc or flange 11 which is affixed to the shaft 9 by screws or bolts 12a and to the conveyor 1 by screws or bolts 12.

The end faces of the conveyor 1 are adjacent to two stationary bearings 17 whose axes are inclined relative to the axis of the conveyor 1. The left-hand bearing 17 surrounds the stationary shaft 7 and is secured to the frame of the filter tipping machine. An elongated key 16 is inserted into matching grooves in the peripheral surface of a sleeve 14 surrounding the shaft 7 and in the internal surface of the left-hand bearing 17. The right-hand bearing 17 of FIG. 1 is mounted on a second stationary sleeve 14 which is attached to the frame of the filter tipping machine by a link 13 and whose peripheral surface has an axially parallel groove for a key 16 also extending into a complementary groove in the internal surface of the right-hand bearing 17. The keys 16 enable the bearings 17 to move nearer to or further away from the conveyor 1, depending upon the length of articles 3 which are to be tested in the improved apparatus. The axes of the cylindrical peripheral surfaces 18 of the bearings 17 make small acute angles with the common axis of the shafts 7 and 9, and the two bearings 17 are mirror symmetrical to each other with reference to a plane which is normal to the axis of the conveyor 1 and is disposed midway between its end faces. The peripheral surfaces 18 are surrounded by antifriction ball or roller bearings 19 for annular carriers 21 each of which can be said to constitute a wobble plate and each of which is coupled to the conveyor 1 so that the conveyor 1 and the two carriers 21 rotate in unison but successive increments of the two carriers either approach or move away from the adjacent end faces of the conveyor during different stages of each revolution. The article 3 which is shown in FIG. 1 is located at the testing station and the inclination of the peripheral surfaces 18 on the stationary bearings 17 is such that successive increments of the carriers 21 are nearest to each other and to the adjacent end faces of the conveyor 1 during travel past the testing station.

The outer sides of the carriers 21 are adjacent to stationary valve plates 22 which are coupled to the respective bearings 17 by links 23. The sealing faces 24 of the valve plates 22 are in permanent sealing engagement with the adjacent portions of the rotating carriers 21, and these valve plates flank the testing station at the twelve o'clock position of the conveyor 1.

The testing apparatus further comprises suitable means (not shown) for releasably locking the bearings 17 to the respective sleeves 14. Such locking means must be disengaged or removed before the bearings 17 can be shifted along the respective keys 16 in order to increase or reduce the distance between the planes of movement of the carriers 21, i.e., to convert the apparatus for the testing of shorter or longer articles.

In accordance with a feature of the invention, the left-hand carrier 21 of FIG. 1 supports an annulus of novel and improved tubular sealing elements 26 each of which can constitute a piece of flexible cylindrical hose and each of which is in register with the article 3 in the adjacent flute 2 of the conveyor 1. The sealing elements 26 can receive the free ends of filter tips 63 of the adjacent articles 3 not later than during travel of such articles and of the respective sealing elements past the testing station. The other end of each article 3 is sealingly engaged by one of an annulus of conventional sealing devices 27 each of which consists of an elastomeric material and may be similar to the sealing devices shown in the patent to Heitmann et al. The sealing devices 27 are designed to engage the end faces of the tobacco-containing portions 63a of the adjacent articles 3 not later than during travel past the testing station.

The sealing elements 26 have outer portions which sealingly surround nipples 28 installed in the left-hand carrier 21 of FIG. 1 and having axial passages which communicate with bores 32 provided in the left-hand carrier 21. The sealing devices 27 are slipped onto similar nipples 28 which are installed in the right-hand carrier 21 and whose passages communicate with bores 32 in the respective carrier. The bores 32 move past and temporarily communicate with arcuate recesses 33 which are machined into the sealing faces 24 of the respective valve plates 22 and which flank (and actually define) the testing station. The recesses 33 of the valve plates 22 communicate with radially outwardly extending channels 29 receiving portions of nipples 31 for admission of testing fluid (e.g., air) by way of a supply conduit 57. The conduit 57 receives testing fluid from a suitable source (not shown) and contains a shutoff valve 61, a preferably adjustable flow restrictor 59 downstream of the valve 61, a pressure gauge 58 downstream of the flow restrictor 59, and additional adjustable flow restrictors 59a immediately upstream of the nipples 31. The length of the recesses 33 does not exceed the distance between two neighboring flutes 2, as considered in the circumferential direction of the conveyor 1. The ends of a cigarette 3 which advances past the testing station between the recesses 33 receive testing fluid from the conduit 57 as long as the respective bores 32 of the carriers 21 communicate with the corresponding recesses 33.

Each sealing device 27 has a front end wall 34 which consists of elastomeric material and has a centrally located aperture 36 for admission of testing fluid into the adjacent end face of the tobacco filler in the respective article 3. As mentioned above, each sealing element 26 can constitute a length of flexible cylindrical hose preferably made of soft rubber or soft elastomeric synthetic plastic material.

In accordance with a feature of the invention, the left-hand carrier 1 of FIG. 1 further supports an annulus of resilient clamping members 37, one for each sealing element 26 and each surrounding the respective sealing element. The clamping members 37 can constitute loops or annuli of plastic or metallic spring wire or metallic or plastic strip stock. The purpose of the clamping members 37 is to ensure that those end portions of the corresponding sealing elements 26 which are surrounded thereby and which, in turn, surround the adjacent ends of articles 3 in the registering flutes 2 during travel past the testing station between the recesses 33 are invariably moved into reliable sealing engagement with the peripheral surfaces of the respective filter tips 63 during those intervals when such filter tips receive testing fluid from the corresponding bores 32.

A first end portion 38 of each clamping member 37 is anchored in or otherwise mounted on the left-hand carrier 21 of FIG. 1, and a second end portion 41 of each clamping member 37 is movable relative to the first end portion 38 to thereby increase or reduce the diameter of the respective clamping member and to thus allow the sealing element 26 within the respective clamping member 37 to expand or to force such sealing element into engagement with the peripheral surface of the article end within the sealing element. The carrier 21 for the sealing elements 26 has slots 39 (FIG. 2) or otherwise configurated cavities for the first end portions 38 of the clamping members 37.

Figure 2:
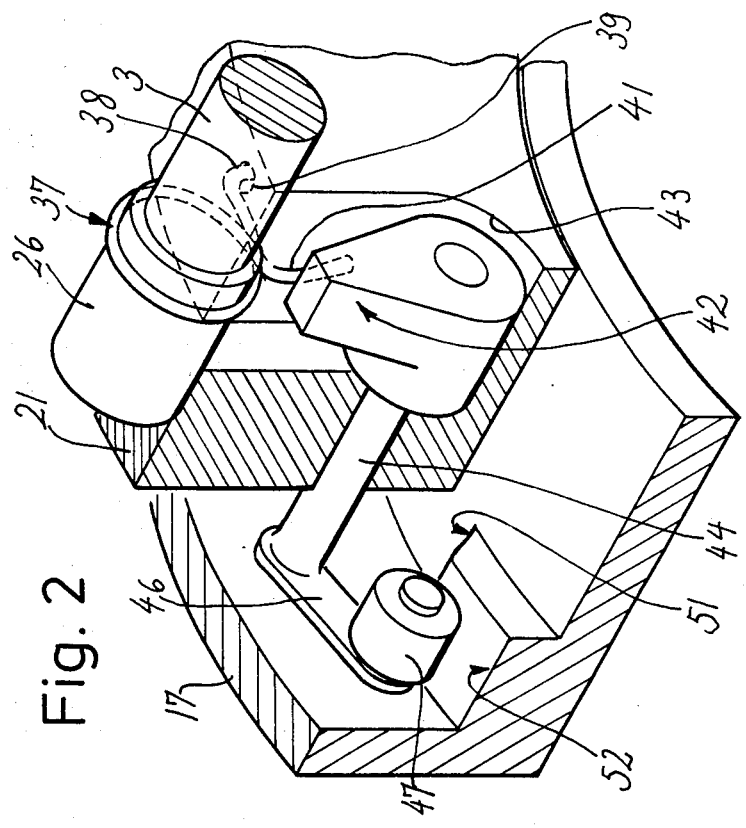
FIG. 2 is an enlarged fragmentary perspective view of a detail in the apparatus of FIG. 1, showing one of the sealing elements, the corresponding clamping member and the actuating means for the clamping member.

The actuating means for moving the second end portions 41 of the clamping members 37 relative to the first end portions 38 during certain stages of each revolution of the left-hand carrier 21 of FIG. 1 comprises cams 42 (one shown on a greatly enlarged scale in FIG. 2) which are pivotable about the axes of shafts 44 and are installed in recesses 43 of the respective carrier 21. The shafts 44 constitute component parts of means for moving (pivoting) the cams 42 relative to the respective carrier 21, and such moving or pivoting means further comprises means for rocking the shafts 44 and their cams 42 back and forth. The rocking means comprises a discrete lever 46 for each shaft 44 (the shafts extend axially outwardly of the respective carrier 21 and the levers 46 are affixed to their exposed ends), a roller follower 47 on each lever 46, and a stationary cam 48 which is provided on the stationary bearing 17 for the left-hand carrier 21 of FIG. 1 and is adjacent to the path of movement of roller followers 47 with the carrier 21. A torsion spring 49 (see FIG. 1) is provided on each shaft 44 outwardly of the respective carrier 21 to bias the corresponding roller follower 47 against the cam 48 on the respective bearing 17. As can be seen in FIG. 2, the stationary cam 48 on the bearing 17 for the left-hand carrier 21 of FIG. 1 comprises a substantially radially inwardly sloping portion 51 along which successive roller followers 47 travel on their way from a raised portion 52 which is tracked while the corresponding cam 42 engages the adjacent second end portion 41 to thus expand the clamping member 37 radially and to allow for radial expansion of the corresponding sealing element 26.

The means for coupling the carriers 21 to the conveyor 1 comprises pins 53 which are anchored in the carriers and extend with clearance into sockets or holes 54 in the adjacent end faces of the conveyor 1. Coil springs 56 are provided to bias the carriers 21 away from the conveyor 1 in order to maintain the carriers in sealing engagement with the faces 24 of the adjacent valve plates 22. The dimensions of the sockets 54 are selected with a view to ensure that the carriers 21 can wobble with reference to the conveyor 1 when the main prime mover of the filter tipping machine drives the shaft 9 which transmits torque to the conveyor. The coil springs 56 are compressed and store energy during movement toward the testing station, and they are allowed to dissipate energy while moving beyond and away from the testing station.

The gauge 58 not only serves to indicate the pressure of testing fluid in the conduit 57 but can also facilitate the task of an operator to adjust the flow restrictor 59 and/or the flow restrictors 59a.

The mode of operation of the apparatus of FIGS. 1 and 2 is as follows:

The prime mover of the filter tipping machine (or another suitable prime mover) drives the shaft 9 which, in turn, drives the conveyor 1 so that the latter can rotate the carriers 21 through the medium of the pins 53. The suction generating device (e.g., a suction pump or a fan) is on so that it draws air from the channel 4 which, in turn, draws air from the channels 6 communicating with flutes 2 which contain or are supposed to contain rod-shaped articles 3. The flutes 2 receive untested articles 3 at a time when they are remote from the testing station (i.e., at a location where the corresponding portions of the two carriers 21 are more distant from one another than at the testing station between the recesses 33 of the valve plates 22). Those portions of the carriers 21 which flank a flute 2 containing a freshly admitted (untested) article 3 thereupon advance toward each other while they continue to rotate with the conveyor 1. This causes the sealing device 27 for such still untested article 3 to move toward and to place its end wall 34 into sealing engagement with the respective end face of the adjacent article 3. At such time, the corresponding sealing element 26 is not compressed or deformed by the associated clamping member 37 so that it is free to permit unimpeded entry of the adjacent end of the filter tip 63. The free end face of such filter tip is located to the left of the corresponding clamping member 37 before the article 3 reaches the testing station. The roller follower 47 of the means for pivoting the cam 42 for such clamping member 37 then moves beyond the raised portion 52 of the cam 48 on the left-hand bearing 17 of FIG. 1 and travels along the sloping surface 51 whereby the second end portion 41 is free to move away from the first end portion 38 due to innate tendency of the clamping member 37 to reduce its diameter. This causes the clamping member 37 to reduce the diameter of the adjacent portion of the sealing element 26 and to deform the latter into pronounced sealing engagement with the peripheral surface of the filter tip 63 which, at such time, extends into the sealing element 26 approaching the testing station between the recesses 33. The roller follower 47 is acted upon by the respective torsion spring 49 to ensure that it remains in contact with the stationary cam 48 which, in turn, ensures that the cam 42 on the respective shaft 44 enables the clamping member 37 to contract into deforming engagement with the respective sealing element 26 during travel past the testing station. It is clear that the operation of the cams 42 would be reversed (and that the configuration of the cam 48 would be changed accordingly) if the clamping members 37 were designed to exhibit a tendency to expand rather than contract. The second free end portions 41 of the clamping members 37 move relative to the corresponding first end portions 38 in planes which are normal to the axes of the respective sealing elements 26. Contraction of the clamping members 37 at the testing station and the resulting deformation of the corresponding sealing elements 26 ensures that the free ends of the filter tips 63 are reliably sealed so that (in the absence of other defects, such open seams and the like), the apparatus can reliably ascertain the permeability of the ventilation zones 62. The pressure gauge 58 or the conduit 57 can contain or can be connected with a suitable transducer which generates signals serving to effect segregation of defective articles 3 from satisfactory articles in a manner which is well known from the art and need not be described here.

The sealing element 26 and the sealing device 27 for the article 3 which has been tested at the station between the recesses 33 thereupon move away from each other to release the freshly tested article and to allow for its removal from the respective flute 2 in a region where the corresponding channels 6 do not communicate with the channel 4 so that the tested article is no longer held by suction and can be readily transferred onto a receiving conveyor whereby the respective flute 2 is free to receive a fresh (untested) article. The roller follower 47 for the corresponding clamping member 37 then tracks the raised portion 52 of the cam 48 so that the clamping member 37 is held in expanded condition (the second end portion 41 is located rather close to the first end portion 38) which ensures that the sealing element 26 does not interfere with the movement of the respective carrier portion away from the adjacent end face of the conveyor 1 while the freshly tested article 3 advances beyond the testing station.

Figure 3:
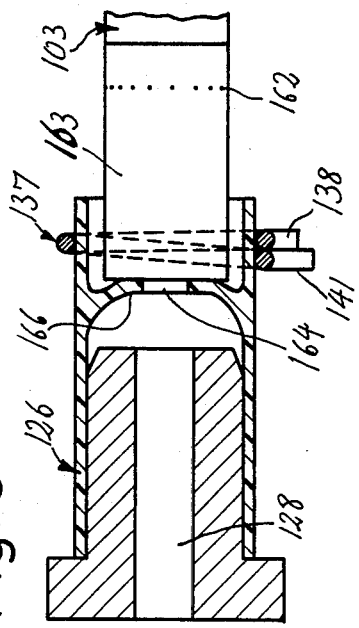
FIG. 3 is an enlarged axial sectional view of a modified sealing element and of the associated clamping member, the free end portion of the sealing element being shown in expanded condition.
Figure 4:
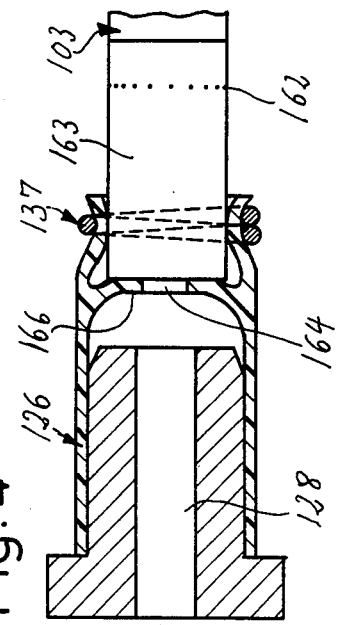
FIG. 4 shows the structure of FIG. 3 but with the free end portion of the sealing element in sealing engagement with the periphery of the rod-shaped article.

FIGS. 3 and 4 illustrate a modified sealing element 126 which is slipped onto a nipple 128 and whose free end portion is surrounded by a clamping member 137, e.g., a clamping member which is identical with the clamping member 37 of FIG. 2. The sealing element 126 contains an internal partition 166 which is formed with a centrally located aperture 164 and whose outer side is engaged by the end face of the filter tip 163 of the respective rod-shaped article 103 at least slightly ahead of the testing station. The ventilation zone of the filter plug 163 is shown at 162. The filter tip 163 begins to bear against the outer side of the partition 166 before the clamping member 137 is permitted or caused to contract (i.e., before it can assume the position which is shown in FIG. 4 and wherein its end portions 138, 141 are more distant from one another than in FIG. 3). This ensures that the apparatus employing sealing elements of the type shown in FIGS. 3 and 4 can test the condition and/or quality of the end faces of filter tips 163. Thus, if the end face of the filter tip 163 is not exactly normal to the axis of the respective article 103, some testing fluid will escape via aperture 164 and along the outer side of the partition 166, and this will be detected by the gauge or by the aforementioned transducer to ensure that the corresponding article is segregated from satisfactory articles.

Actual testing of the wrapper of the article 103 of FIGS. 3 and 4 takes place after the clamping member 137 assumes the position of FIG. 4 in which the adjacent portion of the sealing element 126 is held in sealing engagement with the peripheral surface of the filter tip 163. Thus, the sealing element 126 of FIGS. 3 and 4 allows for two-stage testing of different characteristics of the articles 103. The testing of ventilation zones 162 takes place subsequent to testing of the end faces of the filter tips 163.

An important advantage of the improved testing apparatus is that the means for actuating the clamping members 37 or 137 are not or need not be installed in or on the nipples 28 (such as the nipples and 128) which carry the respective sealing elements 26 or 126. This ensures that such actuating means cannot interfere with the admission of testing fluid into the respective ends of the rod-shaped articles 3 or 103. Moreover, the clamping members 37 or 137 are extremely simple, inexpensive and reliable. If the need arises, they can be replaced with little loss in time and at a minimal cost. As mentioned above, the sealing elements can constitute or resemble conventional hose clamps. Such sealing elements require little or no maintenance, and their useful life is surprisingly long.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. Apparatus for testing rod-shaped articles of the tobacco processing industry wherein an openended tubular wrapper surrounds a filler of tobacco and/or filter material, comprising means for conveying a succession of articles sideways past a testing station, including elongated receiving means for the articles; carrier means adjacent to one end of each of said receiving means and arranged to move with said conveying means; elastically deformable tubular sealing elements provided on said carrier means, one for each of said receiving means and each in register with the adjacent end of the article in the respective receiving means; means for effecting a relative movement between said conveying means and said carrier means so that the ends of articles at said testing station penetrate into the respective sealing elements; substantially annular clamping members, one for each of said sealing elements and each surrounding the respective sealing element; and actuating means for varying the diameters of said clamping members so as urge the respective sealing elements into sealing engagement with the peripheral surfaces of the article ends therewithin during travel of articles past said testing station.

2. The apparatus of claim 1, wherein said clamping members are resilient and exhibit a tendency to contract into deforming engagement with the respective sealing elements, said actuating means including means for effecting radial expansion of said clamping members while such clamping members are remote from the testing station.

3. The apparatus of claim 1, wherein each of said clamping members comprises a first end portion mounted on said carrier means and a second end portion which is movable relative to the first end portion to thereby increase or reduce the diameter of the respective clamping member, said actuating means including means for moving the second end portions of said clamping members relative to the respective first end portions.

4. The apparatus of claim 1, wherein said actuating means comprises a discrete cam for each of said clamping members and means for moving said cams with reference to said carrier means.

5. The apparatus of claim 4, wherein the means for moving said cams comprises shafts, one for each of said cams, and each rotatably journalled in said carrier means, and means for rocking said shafts back and forth in response to movement of said carrier means.

6. The apparatus of claim 5, wherein said rocking means comprises a discrete lever affixed to each of said shafts, a discrete follower on each of said levers, and stationary cam means which is tracked by said followers.

7. The apparatus of claim 1, wherein each of said sealing elements constitutes or includes a length of flexible cylindrical hose.

8. The apparatus of claim 1, wherein each of said sealing elements has an article-receiving open end and an apertured internal partition inwardly spaced from the open end thereof.

9. The apparatus of claim 8, wherein said partitions are arranged to abut against the ends of articles which extend through the open ends of and into the respective sealing elements during travel toward and past said testing station.

10. The apparatus of claim 1, wherein said conveying means and said carrier means are arranged to rotate about mutually inclined axes and said movement effecting means includes a bearing for said carrier means.

* * * * *